(12) United States Patent
Montagnier et al.

(10) Patent No.: US 10,039,777 B2
(45) Date of Patent: Aug. 7, 2018

(54) METHODS AND PHARMACEUTICAL COMPOSITIONS OF THE TREATMENT OF AUTISTIC SYNDROME DISORDERS

(71) Applicant: Luc Montagnier, Paris (FR)

(72) Inventors: Luc Montagnier, New York, NY (US);
Corinne Skorupka, Paris (FR);
Phillipe Raymond, Saint-Peray (FR);
Philippe Bottero, Nyons (FR)

(73) Assignee: NEURO-LM SAS, Le Plessis-Robinson (FR)

( * ) Notice: Subject to any disclaimer, the term of this patent is extended or adjusted under 35 U.S.C. 154(b) by 784 days.

(21) Appl. No.: 14/386,215

(22) PCT Filed: Mar. 20, 2013

(86) PCT No.: PCT/EP2013/055834
§ 371 (c)(1),
(2) Date: Sep. 18, 2014

(87) PCT Pub. No.: WO2013/139861
PCT Pub. Date: Sep. 26, 2013

(65) Prior Publication Data
US 2017/0035792 A1    Feb. 9, 2017

Related U.S. Application Data

(60) Provisional application No. 61/773,016, filed on Mar. 5, 2013.

(30) Foreign Application Priority Data

Mar. 20, 2012  (EP) .................................. 12305326

(51) Int. Cl.
| | | |
|---|---|---|
| *A61K 31/7052* | (2006.01) | |
| *A61K 31/4164* | (2006.01) | |
| *A61K 31/4196* | (2006.01) | |
| *A61K 31/4184* | (2006.01) | |
| *C12Q 1/68* | (2018.01) | |
| *A61K 31/65* | (2006.01) | |
| *C12Q 1/689* | (2018.01) | |

(52) U.S. Cl.
CPC ...... *A61K 31/7052* (2013.01); *A61K 31/4164* (2013.01); *A61K 31/4184* (2013.01); *A61K 31/4196* (2013.01); *A61K 31/65* (2013.01); *C12Q 1/689* (2013.01)

(58) Field of Classification Search
CPC ............ A61K 31/7052; A61K 31/4196; A61K 31/4184; A61K 31/4164; C12Q 1/689
USPC .................................. 424/93.4; 514/2.4, 29
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,458,066 A | 7/1984 | Caruthers et al. |
| 4,683,195 A | 7/1987 | Mullis et al. |
| 4,683,202 A | 7/1987 | Mullis |
| 4,710,384 A | 12/1987 | Rotman |
| 4,861,719 A | 8/1989 | Miller |
| 5,059,595 A | 10/1991 | Le Grazie |
| 5,073,543 A | 12/1991 | Marshall et al. |
| 5,120,548 A | 6/1992 | McClelland et al. |
| 5,236,838 A | 8/1993 | Rasmussen et al. |
| 5,252,479 A | 10/1993 | Srivastava |
| 5,278,056 A | 1/1994 | Bank et al. |
| 5,328,470 A | 7/1994 | Nabel et al. |
| 5,354,556 A | 10/1994 | Sparks et al. |
| 5,391,377 A | 2/1995 | Barnwell |
| 5,458,142 A | 10/1995 | Farmer et al. |
| 5,580,757 A | 12/1996 | Desnick et al. |
| 5,591,767 A | 1/1997 | Mohr et al. |
| 5,639,476 A | 6/1997 | Oshlack et al. |
| 5,674,533 A | 10/1997 | Santus et al. |
| 5,686,311 A | 11/1997 | Shaw |
| 5,721,118 A | 2/1998 | Scheffler |
| 5,733,566 A | 3/1998 | Lewis |
| 5,747,469 A | 5/1998 | Roth et al. |
| 5,879,680 A | 3/1999 | Ginns et al. |
| 5,882,877 A | 3/1999 | Gregory et al. |
| 6,013,516 A | 1/2000 | Verma et al. |
| 6,017,524 A | 1/2000 | Roth et al. |
| 6,025,155 A | 2/2000 | Hadlaczky et al. |
| 6,083,725 A | 7/2000 | Selden et al. |

(Continued)

FOREIGN PATENT DOCUMENTS

| | | |
|---|---|---|
| WO | 94/19478 | 9/1994 |
| WO | 95/14785 | 6/1995 |

(Continued)

OTHER PUBLICATIONS

Bransfield et al. The association between tick-borne infections, Lyme borreliosis and autism spectrum disorders. Medical Hypotheses (2008) 70, 967-974.*

(Continued)

*Primary Examiner* — Yih-Horng Shiao
(74) *Attorney, Agent, or Firm* — Steven M. Hoffberg; Tully Rinckey PLLC

(57) ABSTRACT

The present invention relates to a method for the treatment of an autistic syndrome disorder comprising administering to a subject in need thereof an effective amount of antibacterial agent.

20 Claims, No Drawings

(56) References Cited

U.S. PATENT DOCUMENTS

| | | |
|---|---|---|
| 6,143,290 A | 11/2000 | Zhang et al. |
| 6,187,309 B1 | 2/2001 | McMichael et al. |
| 6,188,045 B1 | 2/2001 | Hansen et al. |
| 6,210,666 B1 | 4/2001 | Miyamura |
| 6,362,226 B2 | 3/2002 | Phillips, III et al. |
| 6,395,884 B1 | 5/2002 | Selden et al. |
| 6,410,010 B1 | 6/2002 | Zhang et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,511,847 B1 | 1/2003 | Zhang et al. |
| 6,632,461 B1 | 10/2003 | Slimak |
| 6,724,188 B2 | 4/2004 | Butters et al. |
| 6,783,757 B2 | 8/2004 | Brudnak |
| 6,952,652 B2 | 10/2005 | Butters |
| 6,998,255 B1 | 2/2006 | Deleersnijder et al. |
| 7,048,906 B2 | 5/2006 | Lin et al. |
| 7,081,747 B2 | 7/2006 | Butters et al. |
| 7,091,182 B2 | 8/2006 | Beck et al. |
| 7,141,573 B2 | 11/2006 | Hanson et al. |
| 7,151,165 B2 | 12/2006 | Venema et al. |
| 7,232,575 B2 | 6/2007 | Walsh et al. |
| 7,252,957 B2 | 8/2007 | Vojdani |
| 7,412,340 B2 | 8/2008 | Butters |
| 7,534,450 B2 | 5/2009 | Walsh et al. |
| 7,575,934 B2 | 8/2009 | Atwood |
| 7,597,936 B2 | 10/2009 | Smith et al. |
| 7,618,658 B2 | 11/2009 | Tsuchida et al. |
| 7,625,704 B2 | 12/2009 | Fredricks et al. |
| 7,682,688 B2 | 3/2010 | Smith |
| 7,709,213 B2 | 5/2010 | Chez |
| 7,718,651 B2 | 5/2010 | White et al. |
| 7,727,561 B2 | 6/2010 | Chan et al. |
| 7,736,622 B2 | 6/2010 | Lin et al. |
| 7,749,509 B2 | 7/2010 | Cobb et al. |
| 7,759,105 B2 | 7/2010 | Cobb et al. |
| 7,763,420 B2 | 7/2010 | Stritzker et al. |
| 7,767,817 B2 | 8/2010 | Wang et al. |
| 7,771,341 B2 | 8/2010 | Rogers |
| 7,820,184 B2 | 10/2010 | Stritzker et al. |
| 7,854,948 B2 | 12/2010 | Slimak |
| 7,880,876 B2 | 2/2011 | Zhao et al. |
| 7,889,334 B2 | 2/2011 | Krause et al. |
| 7,972,601 B2 | 7/2011 | Taylor et al. |
| 7,973,065 B2 | 7/2011 | McClay et al. |
| 7,998,744 B2 | 8/2011 | Stevenson et al. |
| 8,008,036 B2 | 8/2011 | Fallon |
| 8,034,359 B2 | 10/2011 | Gunn |
| 8,048,454 B2 | 11/2011 | Martin |
| 8,075,936 B2 | 12/2011 | Burwell et al. |
| 8,080,269 B2 | 12/2011 | Burwell et al. |
| 8,105,584 B2 | 1/2012 | Fallon |
| 8,110,177 B2 | 2/2012 | Lin et al. |
| 8,163,278 B2 | 4/2012 | Fallon |
| 8,163,566 B2 | 4/2012 | Smith et al. |
| 8,192,733 B2 | 6/2012 | Cobb et al. |
| 8,211,661 B2 | 7/2012 | Fallon |
| 8,304,026 B2 | 11/2012 | Smith et al. |
| 8,334,269 B2 | 12/2012 | Chan et al. |
| 8,354,438 B2 | 1/2013 | Chez |
| 8,367,417 B2 | 2/2013 | Stevenson et al. |
| 8,383,360 B2 | 2/2013 | Van de Water et al. |
| 8,388,935 B2 | 3/2013 | Lin et al. |
| 8,420,096 B2 | 4/2013 | Hawiger et al. |
| 8,431,538 B2 | 4/2013 | Kozikowski et al. |
| 8,501,198 B2 | 8/2013 | Gunn |
| 8,501,463 B2 | 8/2013 | Cox et al. |
| 8,586,115 B2 | 11/2013 | Burwell et al. |
| 8,613,918 B2 | 12/2013 | Fallon |
| 8,653,258 B2 | 2/2014 | Wang et al. |
| 8,673,877 B2 | 3/2014 | Fallon et al. |
| 8,680,072 B2 | 3/2014 | Onsoyen et al. |
| 8,741,957 B2 | 6/2014 | Salvati et al. |
| 8,748,451 B2 | 6/2014 | Kozikowski et al. |
| 8,748,564 B2 | 6/2014 | Wisniewski et al. |
| 8,754,042 B2 | 6/2014 | Prestegarden |
| 8,772,242 B2 | 7/2014 | Borody |
| 8,778,894 B2 | 7/2014 | Tan et al. |
| 8,785,499 B2 | 7/2014 | Mackerell, Jr. et al. |
| 8,810,789 B2 | 8/2014 | Zhao et al. |
| 8,815,233 B2 | 8/2014 | Fallon |
| 8,815,831 B2 | 8/2014 | Onsoyen et al. |
| 8,859,012 B2 | 10/2014 | Chan et al. |
| 8,859,230 B2 | 10/2014 | Ramlov et al. |
| 8,865,406 B2 | 10/2014 | Zhang et al. |
| 8,865,749 B2 | 10/2014 | Marshall |
| 8,871,706 B2 | 10/2014 | Dong et al. |
| 8,876,914 B2 | 11/2014 | Locklin |
| 8,889,358 B2 | 11/2014 | Rudi et al. |
| 8,889,418 B2 | 11/2014 | Zhang et al. |
| 8,895,308 B1 | 11/2014 | Zhang et al. |
| 8,906,918 B1 | 12/2014 | Manetsch et al. |
| 8,940,732 B2 | 1/2015 | Page et al. |
| 8,962,662 B2 | 2/2015 | Busch et al. |
| 8,968,421 B2 | 3/2015 | Locklin |
| 8,975,015 B2 | 3/2015 | McClay et al. |
| 8,980,279 B2 | 3/2015 | Gunn et al. |
| 8,987,246 B2 | 3/2015 | Tierney et al. |
| 9,011,834 B1 | 4/2015 | McKenzie et al. |
| 9,018,158 B2 | 4/2015 | Onsoyen et al. |
| 9,028,841 B2 | 5/2015 | Henn et al. |
| 9,050,276 B2 | 6/2015 | Lipkin et al. |
| 9,056,050 B2 | 6/2015 | Fallon et al. |
| 9,062,086 B2 | 6/2015 | Xie et al. |
| 9,095,545 B2 | 8/2015 | Borody |
| 9,095,713 B2 | 8/2015 | Foster et al. |
| 9,107,864 B2 | 8/2015 | Gunn |
| 9,180,147 B2 | 11/2015 | McKenzie et al. |
| 9,212,204 B2 | 12/2015 | Glass et al. |
| 9,215,877 B2 | 12/2015 | Santra et al. |
| 9,241,511 B2 | 1/2016 | Ramlov et al. |
| 9,249,087 B2 | 2/2016 | Kozikowski et al. |
| 9,320,787 B2 | 4/2016 | Gunn |
| 9,320,788 B2 | 4/2016 | Gunn |
| 9,345,721 B2 | 5/2016 | Fallon et al. |
| 9,347,956 B2 | 5/2016 | Momeni et al. |
| 9,353,156 B2 | 5/2016 | Prestegarden |
| 9,358,276 B2 | 6/2016 | Lin et al. |
| 9,365,611 B2 | 6/2016 | Martinez Botella et al. |
| 9,380,784 B2 | 7/2016 | Derby et al. |
| 2001/0044446 A1 | 11/2001 | Phillips, III et al. |
| 2002/0013270 A1 | 1/2002 | Bolte |
| 2002/0039599 A1 | 4/2002 | Lin et al. |
| 2002/0041871 A1 | 4/2002 | Brudnak |
| 2002/0042357 A1 | 4/2002 | Hanson et al. |
| 2002/0077313 A1 | 6/2002 | Clayman |
| 2002/0155170 A1 | 10/2002 | Walsh et al. |
| 2003/0139341 A1 | 7/2003 | Ramakrishnan |
| 2003/0143590 A1 | 7/2003 | Ramakrishnan |
| 2003/0166600 A1 | 9/2003 | Ramakrishnan |
| 2003/0191061 A1 | 10/2003 | Brewitt |
| 2003/0220259 A1 | 11/2003 | Benner et al. |
| 2004/0024184 A1 | 2/2004 | Kossida |
| 2004/0030100 A1 | 2/2004 | Xiao |
| 2004/0048273 A1 | 3/2004 | Liou |
| 2004/0058350 A1 | 3/2004 | Liou |
| 2004/0062757 A1 | 4/2004 | Finegold |
| 2004/0077041 A1 | 4/2004 | Ramakrishnan |
| 2004/0096847 A1 | 5/2004 | Murakami et al. |
| 2004/0143300 A1 | 7/2004 | Rogers |
| 2004/0170617 A1 | 9/2004 | Finegold |
| 2004/0175407 A1 | 9/2004 | McDaniel |
| 2004/0175796 A1 | 9/2004 | Venema et al. |
| 2004/0213738 A1 | 10/2004 | Croll-Kalish et al. |
| 2004/0213864 A1 | 10/2004 | Slimak |
| 2004/0214863 A1 | 10/2004 | Pratt |
| 2004/0253624 A1 | 12/2004 | Smith et al. |
| 2005/0019259 A1 | 1/2005 | Ausubel et al. |
| 2005/0170333 A1 | 8/2005 | Vojdani |
| 2005/0220910 A1 | 10/2005 | Chan et al. |
| 2005/0238631 A1 | 10/2005 | Burwell |
| 2005/0239720 A1 | 10/2005 | Jenkins |
| 2005/0244515 A1 | 11/2005 | Tsuchida et al. |
| 2005/0245466 A1 | 11/2005 | Jenkins |

(56) References Cited

U.S. PATENT DOCUMENTS

| | | |
|---|---|---|
| 2005/0266529 A1 | 12/2005 | Venema et al. |
| 2005/0271781 A1 | 12/2005 | Burwell et al. |
| 2005/0272122 A1 | 12/2005 | Venema et al. |
| 2005/0272123 A1 | 12/2005 | Venema et al. |
| 2005/0276806 A1 | 12/2005 | Skurkovich et al. |
| 2005/0276872 A1 | 12/2005 | Chan et al. |
| 2006/0025358 A1 | 2/2006 | Marshall |
| 2006/0052428 A1 | 3/2006 | Chez |
| 2006/0110506 A1 | 5/2006 | Burwell et al. |
| 2006/0115467 A1 | 6/2006 | Pangborn et al. |
| 2006/0134397 A1 | 6/2006 | Smith |
| 2006/0147496 A1 | 7/2006 | Lin et al. |
| 2006/0177424 A1 | 8/2006 | Cobb et al. |
| 2006/0182747 A1 | 8/2006 | Skurkovich et al. |
| 2006/0188505 A1 | 8/2006 | Skurkovich et al. |
| 2006/0241103 A1 | 10/2006 | White et al. |
| 2006/0247728 A1 | 11/2006 | Foster et al. |
| 2007/0020343 A1 | 1/2007 | Walsh et al. |
| 2007/0065817 A1 | 3/2007 | Lee et al. |
| 2007/0104733 A1 | 5/2007 | Gunn |
| 2007/0129440 A1 | 6/2007 | Hanson et al. |
| 2007/0134652 A1 | 6/2007 | Slepnev et al. |
| 2007/0135504 A1 | 6/2007 | Marshall |
| 2007/0148136 A1 | 6/2007 | Whitlock |
| 2007/0178495 A1 | 8/2007 | Fredricks et al. |
| 2007/0178541 A1 | 8/2007 | Pedersen et al. |
| 2007/0180544 A1 | 8/2007 | Taylor et al. |
| 2007/0224290 A1 | 9/2007 | Walsh et al. |
| 2007/0274922 A1 | 11/2007 | Wang et al. |
| 2007/0280910 A1 | 12/2007 | Cobb et al. |
| 2007/0280911 A1 | 12/2007 | Cobb et al. |
| 2008/0050718 A1 | 2/2008 | Gesteland et al. |
| 2008/0118913 A1 | 5/2008 | Scott et al. |
| 2008/0167198 A1 | 7/2008 | Cooney et al. |
| 2008/0175923 A1 | 7/2008 | Martin |
| 2008/0193373 A1 | 8/2008 | Stritzker et al. |
| 2008/0254009 A1 | 10/2008 | Finegold |
| 2008/0269116 A1 | 10/2008 | Taub et al. |
| 2008/0305551 A1 | 12/2008 | Chez |
| 2008/0311640 A1 | 12/2008 | Cox et al. |
| 2008/0318871 A1 | 12/2008 | Khan et al. |
| 2009/0011403 A1 | 1/2009 | Smith et al. |
| 2009/0011414 A1 | 1/2009 | Philippi et al. |
| 2009/0074816 A1 | 3/2009 | Gunn |
| 2009/0075274 A1 | 3/2009 | Slepnev et al. |
| 2009/0082220 A1 | 3/2009 | Krause et al. |
| 2009/0112278 A1 | 4/2009 | Wingeier et al. |
| 2009/0126514 A1 | 5/2009 | Burroughs et al. |
| 2009/0130236 A1 | 5/2009 | Tsuchida et al. |
| 2009/0142748 A1 | 6/2009 | Smith et al. |
| 2009/0180987 A1 | 7/2009 | Stritzker et al. |
| 2009/0192165 A1 | 7/2009 | Burwell et al. |
| 2009/0209458 A1 | 8/2009 | Hawiger et al. |
| 2009/0263512 A1 | 10/2009 | Chan et al. |
| 2009/0303472 A1 | 12/2009 | Zhao et al. |
| 2010/0016437 A1 | 1/2010 | Salvati et al. |
| 2010/0029009 A1 | 2/2010 | Stevenson et al. |
| 2010/0087466 A1 | 4/2010 | Sturgess et al. |
| 2010/0113429 A1 | 5/2010 | White et al. |
| 2010/0137249 A1 | 6/2010 | Wang et al. |
| 2010/0167951 A1 | 7/2010 | Lee et al. |
| 2010/0167956 A1 | 7/2010 | Lee et al. |
| 2010/0204169 A1 | 8/2010 | Chan et al. |
| 2010/0209507 A1 | 8/2010 | Lin et al. |
| 2010/0210745 A1 | 8/2010 | McDaniel et al. |
| 2010/0215763 A1 | 8/2010 | Martin |
| 2010/0233146 A1 | 9/2010 | McDaniel |
| 2010/0298304 A1 | 11/2010 | Page et al. |
| 2010/0303782 A1 | 12/2010 | Cobb et al. |
| 2010/0305062 A1 | 12/2010 | Onsoyen et al. |
| 2010/0312045 A1 | 12/2010 | Ramlov et al. |
| 2010/0317677 A1 | 12/2010 | Hassel et al. |
| 2010/0317715 A1 | 12/2010 | Vollrath et al. |
| 2010/0323391 A1 | 12/2010 | Montagnier et al. |
| 2011/0020401 A1 | 1/2011 | Gunn |
| 2011/0037976 A1 | 2/2011 | Zhao et al. |
| 2011/0076710 A1 | 3/2011 | Montagnier |
| 2011/0082180 A1 | 4/2011 | McClay et al. |
| 2011/0091431 A1 | 4/2011 | Olmstead |
| 2011/0104692 A1 | 5/2011 | Rudi et al. |
| 2011/0110942 A1 | 5/2011 | Kallop et al. |
| 2011/0143992 A1 | 6/2011 | Taub et al. |
| 2011/0160133 A1 | 6/2011 | Dong et al. |
| 2011/0165261 A1 | 7/2011 | Derby et al. |
| 2011/0183904 A1 | 7/2011 | Jacobson et al. |
| 2011/0195093 A1 | 8/2011 | Gunn |
| 2011/0201565 A1 | 8/2011 | Tan et al. |
| 2011/0207124 A1 | 8/2011 | Hakonarson et al. |
| 2011/0212435 A1 | 9/2011 | McClay et al. |
| 2011/0269132 A1 | 11/2011 | Stevenson et al. |
| 2011/0281002 A1 | 11/2011 | Burwell et al. |
| 2011/0294384 A1 | 12/2011 | Locklin et al. |
| 2012/0004225 A1 | 1/2012 | Wanaski et al. |
| 2012/0024701 A1 | 2/2012 | Montagnier et al. |
| 2012/0059670 A1 | 3/2012 | Sanborn et al. |
| 2012/0095084 A1 | 4/2012 | Scott et al. |
| 2012/0115803 A1 | 5/2012 | Onsoyen et al. |
| 2012/0122768 A1 | 5/2012 | Onsoyen et al. |
| 2012/0128683 A1 | 5/2012 | Shantha |
| 2012/0129794 A1 | 5/2012 | Dowd et al. |
| 2012/0149872 A1 | 6/2012 | Belgrader |
| 2012/0190708 A1 | 7/2012 | Mackerell, Jr. et al. |
| 2012/0202700 A1 | 8/2012 | Pierson et al. |
| 2012/0202738 A1 | 8/2012 | Borody |
| 2012/0207726 A1 | 8/2012 | Lipkin et al. |
| 2012/0214733 A1 | 8/2012 | Wisniewski et al. |
| 2012/0237994 A1 | 9/2012 | Das et al. |
| 2012/0238468 A1 | 9/2012 | Tuk et al. |
| 2012/0244601 A1 | 9/2012 | Bertozzi et al. |
| 2012/0252740 A1 | 10/2012 | Kozikowski et al. |
| 2012/0252775 A1 | 10/2012 | Finegold |
| 2012/0258135 A1 | 10/2012 | Gunn et al. |
| 2012/0263790 A1 | 10/2012 | Lin et al. |
| 2012/0264758 A1 | 10/2012 | Burwell et al. |
| 2012/0309807 A1 | 12/2012 | Martin |
| 2013/0004477 A1 | 1/2013 | Lu et al. |
| 2013/0005806 A1 | 1/2013 | Beaudet et al. |
| 2013/0022622 A1 | 1/2013 | Ben-Ari et al. |
| 2013/0023461 A1 | 1/2013 | Prestegarden |
| 2013/0036558 A1 | 2/2013 | Locklin |
| 2013/0040519 A1 | 2/2013 | Locklin et al. |
| 2013/0058915 A1 | 3/2013 | Greenberg et al. |
| 2013/0108678 A1 | 5/2013 | Santra |
| 2013/0108702 A1 | 5/2013 | Santra |
| 2013/0128265 A1 | 5/2013 | Zhao et al. |
| 2013/0137732 A1 | 5/2013 | Busch et al. |
| 2013/0143205 A1 | 6/2013 | Montagnier |
| 2013/0177593 A1 | 7/2013 | Gunn et al. |
| 2013/0183680 A1 | 7/2013 | Naides et al. |
| 2013/0184792 A1 | 7/2013 | Simon et al. |
| 2013/0190261 A1 | 7/2013 | Chan et al. |
| 2013/0196939 A1 | 8/2013 | Montagnier |
| 2013/0217000 A1 | 8/2013 | Montagnier |
| 2013/0267441 A1 | 10/2013 | Momeni et al. |
| 2013/0280724 A1 | 10/2013 | Ramadan et al. |
| 2013/0281484 A1 | 10/2013 | Kozikowski et al. |
| 2013/0296430 A1 | 11/2013 | Hardan et al. |
| 2013/0316911 A1 | 11/2013 | Scherer |
| 2013/0317006 A1 | 11/2013 | Yasko |
| 2013/0337012 A1 | 12/2013 | Gunn |
| 2014/0010844 A1 | 1/2014 | Gunn |
| 2014/0024632 A1 | 1/2014 | Tierney et al. |
| 2014/0038913 A1 | 2/2014 | Tan et al. |
| 2014/0065132 A1 | 3/2014 | Hsiao et al. |
| 2014/0080910 A1 | 3/2014 | Ben-Ari et al. |
| 2014/0112940 A1 | 4/2014 | Lane |
| 2014/0112985 A1 | 4/2014 | Bochenek et al. |
| 2014/0128408 A1 | 5/2014 | Kozikowski et al. |
| 2014/0141478 A1 | 5/2014 | Schaffer et al. |
| 2014/0147491 A1 | 5/2014 | Glass et al. |
| 2014/0161721 A1 | 6/2014 | Hatchwell et al. |
| 2014/0162894 A1 | 6/2014 | Hatchwell et al. |
| 2014/0171339 A1 | 6/2014 | Keku et al. |
| 2014/0178948 A1 | 6/2014 | Schaffer et al. |

(56) References Cited

U.S. PATENT DOCUMENTS

| | | |
|---|---|---|
| 2014/0179726 A1 | 6/2014 | Bajaj et al. |
| 2014/0179770 A1 | 6/2014 | Zhang et al. |
| 2014/0179876 A1 | 6/2014 | Locklin |
| 2014/0186905 A1 | 7/2014 | Schaffer et al. |
| 2014/0186919 A1 | 7/2014 | Zhang et al. |
| 2014/0199281 A1 | 7/2014 | Henn et al. |
| 2014/0205643 A1 | 7/2014 | Onsoyen et al. |
| 2014/0206636 A1 | 7/2014 | Lin et al. |
| 2014/0227749 A1 | 8/2014 | Armengaud et al. |
| 2014/0242700 A1 | 8/2014 | Zhang et al. |
| 2014/0242866 A1 | 8/2014 | Locklin |
| 2014/0255384 A1 | 9/2014 | Frey |
| 2014/0256904 A1 | 9/2014 | Schaffer et al. |
| 2014/0273234 A1 | 9/2014 | Zhang et al. |
| 2014/0295556 A1 | 10/2014 | Joung et al. |
| 2014/0295557 A1 | 10/2014 | Joung et al. |
| 2014/0296646 A1 | 10/2014 | Wingeier et al. |
| 2014/0298494 A1 | 10/2014 | Anderson |
| 2014/0302302 A1 | 10/2014 | Locklin |
| 2014/0303243 A1 | 10/2014 | Hakonarson et al. |
| 2014/0314671 A1 | 10/2014 | Namavari et al. |
| 2014/0315992 A1 | 10/2014 | Hakonarson et al. |
| 2014/0328803 A1 | 11/2014 | McKenzie et al. |
| 2014/0335620 A1 | 11/2014 | Zhang et al. |
| 2014/0336181 A1 | 11/2014 | Yasko |
| 2014/0363397 A1 | 12/2014 | Allen-Vercoe et al. |
| 2014/0364373 A1 | 12/2014 | Borody |
| 2015/0037285 A1 | 2/2015 | Blaser et al. |
| 2015/0038407 A1 | 2/2015 | Prestegarden |
| 2015/0038506 A1 | 2/2015 | Nacro et al. |
| 2015/0038577 A1 | 2/2015 | Xie et al. |
| 2015/0079254 A1 | 3/2015 | Ramlov et al. |
| 2015/0080350 A1 | 3/2015 | Partridge et al. |
| 2015/0080409 A1 | 3/2015 | Manetsch et al. |
| 2015/0093360 A1 | 4/2015 | McKenzie et al. |
| 2015/0098974 A1 | 4/2015 | Santra et al. |
| 2015/0111253 A1 | 4/2015 | Schaffer et al. |
| 2015/0111823 A1 | 4/2015 | Dong et al. |
| 2015/0126496 A1 | 5/2015 | Page et al. |
| 2015/0152484 A1 | 6/2015 | Krajmalnik-Brown et al. |
| 2015/0182579 A1 | 7/2015 | Hageman |
| 2015/0190415 A1 | 7/2015 | Lewis et al. |
| 2015/0191607 A1 | 7/2015 | McDaniel |
| 2015/0191765 A1 | 7/2015 | Bassler et al. |
| 2015/0196501 A1 | 7/2015 | Erickson et al. |
| 2015/0197543 A1 | 7/2015 | Glass et al. |
| 2015/0216178 A1 | 8/2015 | Santra et al. |
| 2015/0216806 A1 | 8/2015 | Borody |
| 2015/0219674 A1 | 8/2015 | Hornig et al. |
| 2015/0224164 A1 | 8/2015 | Glass et al. |
| 2015/0227681 A1 | 8/2015 | Courchesne et al. |
| 2015/0232927 A1 | 8/2015 | Sikela |
| 2015/0238589 A1 | 8/2015 | Gunn et al. |
| 2015/0246018 A1 | 9/2015 | Xie et al. |
| 2015/0259728 A1 | 9/2015 | Cutliffe et al. |
| 2015/0272982 A1 | 10/2015 | Hageman |
| 2015/0284434 A1 | 10/2015 | Bissantz et al. |
| 2015/0306152 A1 | 10/2015 | Cani et al. |
| 2015/0306190 A1 | 10/2015 | Lin et al. |
| 2015/0307906 A1 | 10/2015 | Schaffer et al. |
| 2015/0307924 A1 | 10/2015 | Tuk et al. |
| 2015/0322058 A1 | 11/2015 | Bissantz et al. |
| 2015/0328281 A1 | 11/2015 | Borody |
| 2015/0329909 A1 | 11/2015 | Lipkin et al. |
| 2015/0336904 A1 | 11/2015 | Bosmans et al. |
| 2015/0343050 A1 | 12/2015 | Gunn |
| 2015/0353905 A1 | 12/2015 | Weiss et al. |
| 2016/0002620 A1 | 1/2016 | Montagnier |
| 2016/0010076 A1 | 1/2016 | Joung et al. |
| 2016/0017409 A1 | 1/2016 | Flavell et al. |
| 2016/0024523 A1 | 1/2016 | Joung et al. |
| 2016/0024524 A1 | 1/2016 | Joung et al. |
| 2016/0030391 A1 | 2/2016 | Gallagher et al. |
| 2016/0032363 A1 | 2/2016 | Stintzi et al. |
| 2016/0040215 A1 | 2/2016 | Henn et al. |
| 2016/0058056 A1 | 3/2016 | Weaver et al. |
| 2016/0058717 A1 | 3/2016 | Page et al. |
| 2016/0068563 A1 | 3/2016 | Martinez Botella et al. |
| 2016/0068890 A1 | 3/2016 | Pichaud et al. |
| 2016/0075665 A1 | 3/2016 | Page et al. |
| 2016/0083417 A1 | 3/2016 | Martinez Botella et al. |
| 2016/0083418 A1 | 3/2016 | Martinez Botella et al. |
| 2016/0101121 A1 | 4/2016 | Chan et al. |
| 2016/0108080 A1 | 4/2016 | Martinez Botella et al. |
| 2016/0110515 A1 | 4/2016 | Apte et al. |
| 2016/0114322 A1 | 4/2016 | Ismagilov et al. |
| 2016/0120858 A1 | 5/2016 | Kim et al. |
| 2016/0120915 A1 | 5/2016 | Blaser et al. |
| 2016/0120916 A1 | 5/2016 | Hsiao et al. |
| 2016/0120917 A1 | 5/2016 | Bailey et al. |
| 2016/0120920 A1 | 5/2016 | Hsiao et al. |
| 2016/0143961 A1 | 5/2016 | Berry et al. |
| 2016/0143962 A1 | 5/2016 | Berry et al. |
| 2016/0151366 A1 | 6/2016 | Blakely et al. |
| 2016/0153003 A1 | 6/2016 | Joung et al. |
| 2016/0153004 A1 | 6/2016 | Zhang et al. |
| 2016/0158294 A1 | 6/2016 | Von Maltzahn et al. |
| 2016/0158295 A1 | 6/2016 | Afeyan et al. |
| 2016/0175462 A1 | 6/2016 | Zhang et al. |
| 2016/0184370 A1 | 6/2016 | McKenzie et al. |

FOREIGN PATENT DOCUMENTS

| | | |
|---|---|---|
| WO | 96/22378 | 7/1996 |
| WO | WO 01/93904 | * 12/2001 |
| WO | 2006/060414 A2 | 6/2006 |
| WO | 2007/068831 A2 | 6/2007 |
| WO | WO 2010/147714 | * 12/2010 |
| WO | 2013/139861 A1 | 9/2013 |

OTHER PUBLICATIONS

Williams, Brent L., et al. "Application of novel PCR-based methods for detection, quantitation, and phylogenetic characterization of *Sutterella* species in intestinal biopsy samples from children with autism and gastrointestinal disturbances." MBio 3.1 (2012): e00261-11.

Wang, Lv, Claus T. Christophersen, Michael J. Sorich, Jacobus P. Gerber, Manya T. Angley, and Michael A. Conlon. "Increased abundance of *Sutterella* spp. and Ruminococcus torques in feces of children with autism spectrum disorder." Molecular autism 4, No. 1 (2013): 1.

Benach, Jorge L., Ellen Li, and Margaret M. McGovern. "A microbial association with autism." MBio 3, No. 1 (2012): e00019-12.

Midtvedt, Tore. "The gut: a triggering place for autism—possibilities and challenges." Microbial ecology in health and disease 23 (2012).

Krajmalnik-Brown, Rosa, et al. "Gut bacteria in children with autism spectrum disorders: challenges and promise of studying how a complex community influences a complex disease." Microbial ecology in health and disease 26 (2015).

Toh, Michael C., and Emma Allen-Vercoe. "The human gut microbiota with reference to autism spectrum disorder: considering the whole as more than a sum of its parts." Microbial ecology in health and disease 26 (2015).

Frye, Richard E., Stepan Melnyk, and Derrick F. MacFabe. "Unique acyl-carnitine profiles are potential biomarkers for acquired mitochondrial disease in autism spectrum disorder." Translational psychiatry 3.1 (2013): e220.

Son, Joshua S., et al. "Comparison of fecal microbiota in children with autism spectrum disorders and neurotypical siblings in the simons simplex collection." PloS one 1010 (2015): e0137725.

Samsam, Mohtashem, Raheleh Ahangari, and Saleh A. Naser. "Pathophysiology of autism spectrum disorders: Revisiting gastrointestinal involvement and immune imbalance." World journal of gastroenterology: WJG 20.29 (2014): 9942.

De Theije, Caroline GM, et al. "Altered gut microbiota and activity in a murine model of autism spectrum disorders." Brain, behavior, and immunity 37 (2014): 197-206.

(56) References Cited

OTHER PUBLICATIONS

Reddy, Bhaskara Lakshmi, and Milton H. Saier. "Autism and Our Intestinal Microbiota." Journal of molecular microbiology and biotechnology 25.1 (2015): 51-55.
Mangiola, Francesca, et al. "Gut microbiota in autism and mood disorders." World journal of gastroenterology 22.1 (2016): 361.
Rodakis, John. "An n=1 case report of a child with autism improving on antibiotics and a father's quest to understand what it may mean." Microbial ecology in health and disease 26 (2015).
Patterson, Paul H. Novel Probiotic Therapies for Autism. California Inst of Tech Pasadena, 2013.
Sajdel-Sulkowska, Elizabeth M., and Romuald Zabielski. Gut Microbiome and Brain-Gut Axis in Autism—Aberrant Development of Gut-Brain Communication and Reward Circuitry. INTECH Open Access Publisher, 2013.
Louis, Petra. "Does the human gut microbiota contribute to the etiology of autism spectrum disorders?." Digestive diseases and sciences (2012): 1-3.
De Angelis, Maria, Maria Piccolo, Lucia Vannini, Sonya Siragusa, Andrea De Giacomo, Diana Isabella Serrazzanetti, Fernanda Cristofori, Maria Elisabetta Guerzoni, Marco Gobbetti, and Ruggiero Francavilla. "Fecal microbiota and metabolome of children with autism and pervasive developmental disorder not otherwise specified." PLoS One 8, No. 10 (2013): e76993.
Grossi, E., and V. Terruzzi. "The role of intestinal dysbiosis in the pathogenesis of autism: minireview." Int J Microbiol Adv Immunol 2(2) (2014): 41-44.
Hsiao, Elaine Y. "Gastrointestinal issues in autism spectrum disorder." Harvard review of psychiatry 22.2 (2014): 104-111.
Siniscalco, Dario. "Autism-Open Access." (2015). http://www.esciencecentral.org/journals/gut-bacteriabrain-axis-in-autism-2165-7890.1000e124.pdf.
Cao, Xinyi, Ping Lin, Ping Jiang, and Chunbo Li. "Characteristics of the gastrointestinal microbiome in children with autism spectrum disorder: a systematic review." Shanghai Arch Psychiatry 25, No. 6 (2013): 342-353.

Harumi Jyonouchi, Lee Geng, Deanna L Streck and Gokce A Toruner, "Immunological characterization and transcription profiling of peripheral blood (PB) monocytes in children with autism spectrum disorders (ASD) and specific polysaccharide antibody deficiency (SPAD): case study", Jyonouchi et al. Journal of Neuroinflammation 2012, 9:4, http://www.jneuroinflammation.com/content/9/1/4 (2012).
Hiroshi Sakon, Fumiko Nagai, Masami Morotomi and Ryuichiro Tanaka, "*Sutterella parvirubra* sp. nov. and *Megamonas funiformis* sp. nov., isolated from human faeces", International Journal of Systematic and Evolutionary Microbiology (2008), 58, 970-975 DOI 10.1099/ijs.0.65456-0.
Kang, Dae-Wook, et al. "Reduced incidence of Prevotella and other fermenters in intestinal microflora of autistic ahildren." PLoS One 8.7 (2013): e68322.
Wrong, What Can Go. "Posts Tagged 'autism'." (Downloaded Jan. 28, 2016).
Ming, Xue, et al. "Metabolic perturbance in autism spectrum disorders: a metabolomics study." Journal of proteome research Nov. 12, 2012: 5856-5862.
Heberling, Colin, and Prasad Dhurjati. "Novel Systems Modeling Methodology in Comparative Microbial Metabolomics: Identifying Key Enzymes and Metabolites Implicated in Autism Spectrum Disorders." International journal of molecular sciences 16.4 (2015): 8949-8967.
Ts, Ignatova-Ivanova, et al. "Foods and Social Problems in Children With Autism Spectrum Disorders." Global Journal of Arts, Humanities and Social Sciences, vol. 3, No. 10, pp. 17-24, Oct. 2015.
Autism, Treating. "Medical Comorbidities in Autism Spectrum Disorders." (2013).
International Search Report for PCT/FR2006/002735 dated Jul. 8, 2008.
International Preliminary Report on Patentability for PCT/FR2006/002735 dated Jun. 18, 2008.

\* cited by examiner

METHODS AND PHARMACEUTICAL COMPOSITIONS OF THE TREATMENT OF AUTISTIC SYNDROME DISORDERS

CROSS REFERENCE TO RELATED APPLICATIONS

The present application is a U.S. National Stage application under 35 U.S.C. § 371, claiming benefit of priority under 35 U.S.C. § 365 from PCT/EP2013/055834, which claims benefit of priority from EP 1230532.6, filed Mar. 20, 2012, and U.S. Provisional Patent Application No. 61/773, 016, filed Mar. 5, 2013, each of which is expressly incorporated herein in its entirety.

FIELD OF THE INVENTION

The present invention relates to methods and pharmaceutical compositions for the treatment of Autistic Syndrome Disorders.

BACKGROUND OF THE INVENTION

Infantile Autistic Syndrome Disorders (ASD) include a wide range of abnormalities including a genuine incapacity to organize affective relations, behavioral anomalies in reciprocal social interactions, verbal and non-verbal communication, limited interest in the surrounding environment associated with stereotyped movements and repetitive plays (Kanner, 1943; Levy and Hyman, 1993; Levy and Hyman, 2005; Adrien et al., 2001; Blanc et al., 2005; Bourreau et al., 2009). Research to date indicates that a genetic predisposition may play a role in the disease but one or more environmental factors must be in place for symptoms to occur including environmental contaminants and possibly maternal exposures during gestation (Persico and Bourgeron, 2006; Bourgeron, 2009; Patterson, 2002). It is suggested that genetic and environmental hazards will alter developmental programs leading to cortical and/or subcortical malformations and the formation of misplaced/ misconnected neuronal ensembles. The first symptoms occur before 3 years of age with most likely an earlier origin. There is at present no efficient biological/pharmaceutical treatment to ASD.

SUMMARY OF THE INVENTION

The present invention relates to a method for the treatment of an autistic syndrome disorder comprising administering to a subject in need thereof with an effective amount of at least one antibacterial agent.

DETAILED DESCRIPTION OF THE INVENTION

The present invention relates to a method for the treatment of an autistic syndrome disorder comprising administering to a subject in need thereof with an effective amount of at least one antibacterial agent.

In a particular embodiment, the subject is diagnosed with autism. As used herein, the term "autism" denotes a family of disorders of neural development that is characterized by impaired social interaction and communication, restricted and repetitive behavior accompanied with other deficits. These signs all begin before a child is three years old.

Autism affects information processing in the brain by altering how nerve cells and their synapses connect and organize; how this occurs is not well understood. The two other autism spectrum disorders (ASD) are Asperger syndrome, which lacks delays in cognitive development and language, atypical autism, diagnosed when full criteria for the other two disorders are not met, and PDD-NOS when pervasive developmental disorder are not specified.

In a particular embodiment, the subject has been previously diagnosed with a latent bacterial infection. Typically said latent bacterial infection may be detected by detecting the presence of bacterial 16S sequence in a blood sample obtained from the subject (e.g. by RT-PCR) or by performing the method as described in WO2007068831 or in US2012024701 in the blood sample, such as described in EXAMPLE 1 or 2.

As used herein the term "antibacterial agent" has its general meaning in the art. Antibacterial agents kill or inhibit the growth or function of bacteria. A large class of antibacterial agents is antibiotics. Any kind of antibiotics may be used according to the invention, but use of broad-spectrum antibiotics are particularly desirable. A broad spectrum antibiotic for use in the invention is one that possesses activity against both gram-positive and gram-negative organisms. Exemplary broad spectrum antibiotics for use in the invention include compounds falling within the following chemical classifications or categories: aminoglycosides, macrolides, ketolides, quinolones, tetracyclines, sulfonamides, and beta-lactams (including the cephalosporins). In yet another embodiment, a broad spectrum antibiotic for use in the invention is one demonstrating a degree of antimicrobial activity comparable to that of any of the herein described aminoglycosides, macrolides, ketolides, quinolones, tetracyclines, sulfonamides, or beta-lactams, in particular, against species falling within four or more different microbial genuses selected from *Actinomyces, Bacillus, Bordetella, Borrelia, Campylobacter, Chlamydia, Clostridium, Corynebacterium, Cryptosporidium, Entamoeba, Enterobacter, Escherichia, Gardnerella, Haemophilus, Klebsiella, Legionella, Leishmania, Moraxella, Mycobacterium, Mycoplasma, Neisseria, Nocardia, Proteus, Providencia, Pseudomonas, Salmonella, Serpulina, Serratia, Shigella, Staphylococcus, Streptococcus, Suterella, Toxoplasmosis, Treponem*, and *Tubercle*.

The first type of broad spectrum for use in the invention, are tetracyclines. Tetracyclines belong to a class that shares a four-membered ring structure composed of four fused 6-membered (hexacyclic) rings. The tetracyclines exhibit their activity by inhibiting the binding of the aminoacyl tRNA to the 30S ribosomal subunit in susceptible bacteria. Tetracyclines for use in the invention include chlortetracycline, demeclocycline, doxycycline, minocycline, oxytetracycline, chlortetracycline, methacycline, mecocycline, tigecycline, limecycline, and tetracycline. The tetracyclines are effective against many known organisms including α-hemolytic streptococci, nonhemolytic streptococci, gram-negative bacilli, rickettsiae, spirochetes, *Mycoplasma*, and *Chlamydia*.

Another type of broad spectrum antibiotics for use in the invention is the aminoglycosides. Aminoglycosides are compounds derived from species of *Streptomyces* or *Micomonospora* bacteria and are primarily used to treat infections caused by gram-negative bacteria. Drugs belonging to this class all possess the same basic chemical structure, i.e., a central hexose or diaminohexose molecule to which two or more amino sugars are attached by a glycosidic bond. The aminoglycosides are bactericidal that bind to the 30S ribosome and inhibit bacterial protein synthesis. They are active primarily against aerobic gram-negative bacilli and staphylococci. Aminoglycoside for use in the invention include amikacin (Amikin®), gentamicin (Garamycin®), kanamycin (Kantrex®), neomycin (Mycifradin®), netilmicin (Netromycin®), paromomycin (Humatin®), streptomycin, and tobramycin (TOBI Solution®, TobraDex®).

Yet another type of broad spectrum antibiotic for use in the invention is a macrolide. The macrolides are a group of polyketide antibiotic drugs whose activity stems from the presence of a ring (a large 14-, 15-, or 16-membered lactone ring) to which one or more deoxy sugars, usually cladinose and desosamine, are attached. Macrolides are primarily bacteriostatic and bind to the 50S subunit of the ribosome, thereby inhibiting bacterial synthesis. Macrolides are active against aerobic and anaerobic gram positive cocci (with the exception of enterococci) and against gram-negative anaerobes. Macrolides for use in the invention include azithromycin (Zithromax®), clarithromycin (Biaxin®), dirithromycin (Dynabac®), erythromycin, clindamycin, josamycin, roxithromycin and lincomycin.

Also suitable for use in the present invention are the ketolides, another type of broad spectrum antibiotic. The ketolides belong to a new class of semi-synthetic 14-membered ring macrolides in which the erythromycin macrolactone ring structure and the D-desosamine sugar attached at position 5 are retained, however, replacing the L-cladinose moiety and hydroxyl group at position 3 is a 3-keto functional group. The ketolides bind to the 23S rRNA, and their mechanism of action is similar to that of macrolides (Zhanel, G. G., et al., *Drugs,* 2001; 61(4):443-98). The ketolides exhibit good activity against gram-positive aerobes and some gram-negative aerobes, and possess excellent activity against *Streptococcus* spp. Including mefA and ermB-producing *Streptococcus pneumoniae,* and *Haemophilus influenzae.* Representative ketolides for use in the invention include telithromycin (formerly known as HMR-3647), HMR 3004, HMR 3647, cethromycin, EDP-420, and ABT-773.

Yet another type of broad spectrum antibiotic for use in the invention is the quinolone class. Structurally, the quinonolones possess a 1,4 dihydro-4-oxo-quinolinyl moiety bearing an essential carboxyl group at position 3. Functionally, the quinolones inhibit prokaryotic type II topoisomerases, namely DNA gyrase and, in a few cases, topoisomerase IV, through direct binding to the bacterial chromosome. Quinolones for use in the invention span first, second, third and fourth generation quinolones, including fluoroquinolones. Such compounds include nalidixic acid, cinoxacin, oxolinic acid, flumequine, pipemidic acid, rosoxacin, norfloxacin, lomefloxacin, ofloxacin, enrofloxacin, ciprofloxacin, enoxacin, amifloxacin, fleroxacin, gatifloxacin, gemifloxacin, clinafloxacin, sitafloxacin, pefloxacin, rufloxacin, sparfloxacin, temafloxacin, tosufloxacin, grepafloxacin, levofloxacin, moxifloxacin, and trovafloxacin. Additional quinolones suitable for use in the invention include those described in Hooper, D., and Rubinstein, E., "*Quinolone Antimicrobial Agents, Vd Edition*", American Society of Microbiology Press, Washington D.C. (2004).

A broad spectrum antibiotic for use in the invention may also be a sulfonamide. Drugs belonging to the sulfonamide class all possess a sulfonamide moiety, $-SO_2NH_2$, or a substituted sulfonamide moiety, where one of the hydrogens on the nitrogen is replaced by an organic substituent. Illustrative N-substituents include substituted or unsubstituted thiazole, pyrimidine, isoxazole, and other functional groups. Sulfonamide antibiotics all share a common structural feature, i.e., they are all benzene sulfonamides, meaning that the sulfonamide functionality is directly attached to a benzene ring. The structure of sulfonamide antibiotics is similar to p-aminobenzoic acid (PABA), a compound that is needed in bacteria as a substrate for the enzyme, dihydroptroate synthetase, for the synthesis of tetrahydro-folic acid. The sulfonamides function as by interfering with the metabolic processes in bacteria that require PABA, thereby inhibiting bacterial growth and activity. Sulfonamide antibiotics for use in the invention include the following: mafenide, phtalylsulfathiazole, succinylsulfathiazole, sulfacetamide, sulfadiazine, sulfadoxine, sulfamazone, sulfamethazine, sulfamethoxazole, sulfametopirazine, sulfametoxypiridazine, sulfametrol, sulfamonomethoxine, sulfamylon, sulfanilamide, sulfaquinoxaline, sulfasalazine, sulfathiazole, sulfisoxazole, sulfisoxazole diolamine, and sulfaguanidine.

Also suitable for use in the invention are the broad spectrum antibiotics classified structurally as beta-lactams. All members of this broad spectrum class possess a beta-lactam ring and a carboxyl group, resulting in similarities in both their pharmacokinetics and mechanism of action. The majority of clinically useful beta-lactams belong to either the penicillin group or the cephalosporin group, including cefamycins and oxacephems. The beta-lactams also include the carbapenems and monobactams. Generally speaking, beta-lactams inhibit bacterial cell wall synthesis. More specifically, these antibiotics cause 'nicks' in the peptidoglycan net of the cell wall that allow the bacterial protoplasm to flow from its protective net into the surrounding hypotonic medium. Fluid then accumulates in the naked protoplast (a cell devoid of its wall), and it eventually bursts, leading to death of the organism. Mechanistically, beta-lactams act by inhibiting D-alanyl-D-alanine transpeptidase activity by forming stable esters with the carboxyl of the open lactam ring attached to the hydroxyl group of the enzyme target site. Beta-lactams are extremely effective and typically are of low toxicity. As a group, these drugs are active against many grampositive, gram-negative and anaerobic organisms. Drugs falling into this category include 2-(3-alanyl)clavam, 2-hydroxymethylclavam, 7-methoxycephalosporin, epithienamycin, acetyl-thienamycin, amoxicillin, apalcillin, aspoxicillin, azidocillin, azlocillin, aztreonam, bacampicillin, blapenem, carbenicillin, carfecillin, carindacillin, carpetimycin A and B, cefacetril, cefaclor, cefadroxil, cefalexin, cefaloglycin, cefaloridine, cefalotin, cefamandole, cefapirin, cefatrizine, cefazedone, cefazolin, cefbuperazone, cefcapene, cefdinir, cefditoren, cefepime, cefetamet, cefixime, cefinenoxime, cefinetazole, cefminox, cefmolexin, cefodizime, cefonicid, cefoperazone, ceforamide, cefoselis, cefotaxime, cefotetan, cefotiam, cefoxitin, cefozopran, cefpiramide, cefpirome, cefpodoxime, cefprozil, cefquinome, cefradine, cefroxadine, cefsulodin, ceftazidime, cefteram, ceftezole, ceftibuten, ceftizoxime, ceftriaxone, cefuroxime, cephalosporin C, cephamycinA, cephamycinC, cephalothin, chitinovorin A, chitinovorin B, chitinovorin C, ciclacillin, clavulanate salt, clavulanic acid, clometocillin, cloxacillin, cycloserine, deoxy pluracidomycin B and C, dicloxacillin, dihydro pluracidomycin C, epicillin, epithienamycin D, E, and F, ertapenem, faropenem, flomoxef, flucloxacillin, hetacillin, imipenem, lenampicillin, loracarbef, mecillinam, meropenem, metampicillin, meticillin (also referred to as methicillin), mezlocillin, moxalactam, nafcillin, northienamycin, oxacillin, panipenem, penamecillin, penicillin G, N, and V, phenethicillin, piperacillin, povampicillin, pivcefalexin, povmecillinam, prvmecillinam, pluracidomycin B, C, and D, propicillin, sarmoxicillin, sulbactam, sultamicillin, talampicillin, temocillin, terconazole, thienamycin, andticarcillin.

By "an effective amount" is meant a sufficient amount of the antibacterial agent to for treating autism at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

A combination of antibacterial agents (e.g. antibiotics) is encompassed by the present invention.

In a particular embodiment, the subjected undergoes a sustained administration with the antibacterial agent. Typically, the subject is administered with the antibacterial agent for 1, 2, 3, 4 or 5 weeks.

In a particular embodiment, the subject may also be administered with antifungal agents or anti-parasitic agents.

In a particular embodiment, the subject is administered with the antibacterial agent optionally in combination with anti-fungal or anti-parasitic agents following the typical regimen: for 3 weeks per month during the 3 first months of treatment, then 15 days per month during the following three months, then 15 days every 2 months during the following 6 months and finally 3 or 4 courses of 10 days treatment the following years.

The antibacterial agent may be combined with pharmaceutically acceptable excipients, and optionally sustained-release matrices, such as biodegradable polymers, to form pharmaceutical compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antibacterial agent of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the antibiotic(s) in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The antibacterial agent of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples.

However, these examples and figures should not be interpreted in any way as limiting the scope of the present invention.

EXAMPLE 1

The technology as described in WO2007068831 or in US2012024701 allows the detection of aqueous structures induced by certain DNA molecules that emit low frequency electromagnetic signals. These DNA sequences "sensors" are present in most bacteria potentially pathogenic in humans and induce nanostructures present in blood plasma or in certain dilutions of DNA extracted from plasma or blood cells. By performing said method the inventors demonstrate that detection of a latent bacterial infection (but not viral infection) can be made for 70 to 90% of autistic children who were included in the study. Interestingly, in a blind study, the sole autistic child that were considered as negative for the presence of a latent bacterial infection was treated with antibiotics in a long-term manner. In another example, a child who had low frequency electromagnetic signals saw them reduced after treatment and clinical improvement.

This correlation between disappearance of the low frequency electromagnetic signals of bacterial and clinical improvement on antibiotics shows that the infection is not a simple consequence but is one of the causes of autism and low frequency electromagnetic signal detection can serve as a biomarker in clinical trials.

EXAMPLE 2

Autism: The Gut-blood-brain Connection:
Improved Methods for the Detection and
Diagnostic of Abnormal Bacteremia in Autistic
Patients Within a decade, autism and its related disorders have become a major health problem worldwide. In most developed and even in developing countries, their incidence has been growing to more than 1% of the total child population.

The reason for this continuous increase is unclear, but cannot be ascribed to genetic changes suddenly affecting the new generations. Rather, the increased exposure to changing environmental factors may be involved.

There is mounting indication that these environmental changes occurring at the intestinal level may allow the abnormal passage of bacteria or bacterial products in the blood circulation which could then reach the brain. There is also evidence that the blood-brain barrier can become more permeable, due also to environmental changes.

Recently, the group of Williams and Lipkin has described a significant increase of a particular genus belonging to a Gram negative family (Alcaligenaceae), the bacteria *Sutterella*, in ileal biopsies of autistic children suffering from gastro-intestinal disturbance, as opposed to non-autistic children suffering of the same affection.

The present example describes the abnormal presence of bacterial DNA in the blood of the majority of autistic children studied, and in particular of bacterial DNA identical or close to that of the *Sutterella* genus.

This bacterial DNA is reduced by a long term antibiotic treatment of children which improves at the same time their clinical condition (example 3).

The detection of bacterial DNA is done by the use of two technologies:

a) One has already been described in several patent applications (WO2007068831 or in US2012024701).

In short, it consists in measuring the intensity of the electromagnetic signals emitted by some high water dilutions of DNA extracted from the plasma of such patients.

This DNA may originate from bacterial or viral DNA sequences. Filtration of the DNA solution by 100 nM porosity filters allows one to detect structures derived from bacterial DNA.

Filtration at 20 nM porosity allows one to detect small structures derived from DNA of small DNA viruses and HIV DNA.

In the case of autistic patients, we have found that a majority of those who do possess in their plasma some DNA sequences inducing nanostructures able to emit EMS. Since filtration at 100 nM was required, these nanostructures are presumed to be of bacterial origin.

This technology, in its present state, does not yet permit us to distinguish between bacterial species since the signals are similar.

However there are indications that the signals also contain the specific information for transmitting particular DNA sequences. This phenomenon has been reproduced in several independent laboratories.

b) the classical technology, Polymerase Chain Reaction (PCR) to identify the species of bacteria involved.

In a first approach, we used primers able to detect all types of Gram positive bacteria which yielded a majority of positive signals in a cohort of 22 autistic children but not in the same number of healthy children of matching age.

We also designed primers to recognize the group of Gram negative bacteria, based also on the 16 S ribosomal DNA. However our controls with pure sterile water were always positive due to the presence of small fragments contaminating bacterial DNA in various samples of that water, whatever its treatment.

Finally we used primers specific for the *Sutterella* genus and have clear-cut results: a large majority of the plasma of autistic children yielded a specific DNA band of the required size (260 bp) and sequencing of the bands confirm that they belong to two closely related families (Alcaligenaceae and Burkholderiaceae). Less frequently, we could detect *Borrelia* sequences, the agent of Lyme disease, by primers specific for its 16 S ribosomal DNA.

TABLE A

Distribution of EMS and Sutterella PCR in Autistic Children and healthy controls (French-Italian cohort)

|  |  | EMS |  | PCR Suterrella |  |
| --- | --- | --- | --- | --- | --- |
|  | n | + | − | + | − |
| Autistic children | 78 | 68 (87%) | 10 (13%) | 65 (83%) | 13 (17%) |
| Controls | 28 | 1 (3.5%) | 27 (96.5%) | 3 (10%) | 25 (89%) |

Legend:
EMS = Electromagnetic Signals
N = Number of patients
PCR = Polymerase Chain Reaction.

EXAMPLE 3

Clinical Study

Study: 97 children were included in the study: children diagnosed with autism (n=73), atypical autism (n=10), Dravet syndrome (n=4), Rett syndrome (n=2), Asperger syndrome (n=3), epilepsy with mental retardation (n=3) and Gilles de la Tourette syndrome (n=2). 88% of the children were aged between 2.5 years old and 12 years old (min=15 months old and max =29 years old). The children received administration of broad spectrum antibiotics for 3 weeks: for children older than 8 years old with macrolides and children older less than 8 years with tetracyclines. Furthermore, the children received an antifungal agent (Triflucan) and antiparasitic agents (Fluvermal and Flagyl). Nutritional and immunological deficiencies were also corrected.

Results: The treatment was interrupted for 17% of the children due to side effects. Slow or jagged progression was observed for 28% of the children. Rapid and regular progression was observed for 55% of the children (Tables 1 and 2). More particularly, in the first month, improvement in physical signs can be noticed. In a second time, behavioral symptoms are improved in a progressive manner. In a third time, mental progression resumed its course to where it was interrupted (psychomotrocity, learning, communication, and language and graphics). Administration of antibiotics, regular at the beginning, may become common. In some cases, the clinical improvement obtained is durable and persists after cessation of treatment.

TABLE 1

|  | Rapid Progress | Slow Progress | Insufficient Progress | Treatment interrupted |
| --- | --- | --- | --- | --- |
| Autism (n = 73) | 41 (56%) | 19 (26%) | 8 (11%) | 5 (7%) |
| Atypical (n = 100) | 7 | 3 |  |  |
| Dravet (EMSN) (n = 4) | 2 | 2 |  |  |
| Rett (n = 2) | 1 | 1 |  |  |
| Epilepsy with mental retardation (n = 3) | 1 | 1 | 1 |  |
| Asperger (n = 3) |  |  | 3 |  |
| Gilles de la Tourette syndrome (n = 2) | 1 | 1 | 3 |  |
| TOTAL = 97 | 53 (55%) | 27 (28%) | 12 (12%) | 5 (5%) |

TABLE 2

|  | Rapid Progress | Slow Progress | Insufficient Progress | Treatment interrupted |
| --- | --- | --- | --- | --- |
| Autistic children ≤ 7 years old (n = 45) | 32 (71%) | 6 (13%) | 3 (7%) | 4 (9%) |
| Autistic children > 7 years old (n = 9) | 9 (32%) | 13 (46%) | 5 (18%) | 1 (4%) |

REFERENCES

Throughout this application, various references describe the state of the art to which this invention pertains. The disclosures of these references are hereby incorporated by reference into the present disclosure.

Adrien J L, Rossignol-Deletang N, Martineau J, Couturier G, Barthelemy C (2001) Regulation of cognitive activity and early communication development in young autistic, mentally retarded, and young normal children. Dev Psychobiol 39:124-136.

Blanc R, Adrien J L, Roux S, Barthelemy C (2005) Dysregulation of pretend play and communication development in children with autism. Autism 9:229-245.

Bourgeron T (2009) A synaptic trek to autism. Curr Opin Neurobiol 19:231-234.

Bourreau Y., Roux S., Gomot M., Bonnet-Brilhault F., Barthelemy C. (2009) Validation of the repetitive and restricted behaviour scale in autism spectrum disorders. European Child and adolescent psychiatry, Nov 18(11): 675-682.

Kanner L. (1943) Autistic disturbances of affective contact. Nervous Child 2: 217-50

Levy S E, Hyman SL (1993) Pediatric assessment of the child with developmental delay. Pediatr Clin North Am 40:465-477.

Levy S E, Hyman S L (2005) Novel treatments for autistic spectrum disorders. Ment Retard Dev Disabil Res Rev 11:131-142.

Patterson P H (2002) Maternal infection: window on neuroimmune interactions in fetal brain development and mental illness. Curr Opin Neurobiol12:115-118.

Persico A M, Bourgeron T (2006) Searching for ways out of the autism maze: genetic, epigenetic and environmental clues. Trends Neurosci 29:349-358.

The invention claimed is:

1. A method for the treatment of an autistic spectrum disorder, consisting of:
   detecting a bacterial infection by bacteria of at least one of genus *Sutterella* and genus *Borrelia*, in a person with autistic spectrum disorder;
   administering to the person with autistic spectrum disorder, a course of therapy comprising an effective amount of at least one antibacterial agent adapted to suppress the bacteria of at least one of genus *Sutterella* and genus *Borrelia*, and at least one antiparasitic drug for 3 weeks per month during the first 3 months of the course of therapy; and
   during said administration, monitoring symptoms of the autistic spectrum disorder in the person.

2. The method according to claim 1, wherein said detecting comprises performing a polymerase chain reaction amplification using primers specific for bacteria of at least one of genus *Suterella* and genus *Borrelia*.

3. A method of treating an autistic spectrum disorder patient, consisting of:
   determining presence of a bacterial infection with an intestinal bacteria of genus *Sutterella* and/or *Borrelia* in the patient;
   coadministering at least one antibiotic having a spectrum of activity against genus *Sutterella* and/or *Borrelia* bacteria and at least one antiparasitic drug, and optionally at least one antifungal drug, for 3 weeks per month during the first 3 months of coadministration;
   monitoring autistic behaviors of the patient; and
   interrupting administration of the at least one antibiotic and the at least one antiparasitic drug after clinical improvement is obtained.

4. The method according to claim 3, wherein the at least one antibiotic comprises a tetracycline or a macrolide.

5. The method according to claim 4, wherein the macrolide comprises azithromycin.

6. The method according to claim 3, wherein the method comprises coadministering at least one antifungal drug with the at least one antibiotic and the at least one antiparasitic drug.

7. The method according to claim 6, wherein the at least one fungal drug comprises fluconazole.

8. The method according to claim 3, wherein said determining comprises performing a polymerase chain reaction amplification using primers specific for bacteria of at least one of genus *Suterella* and genus *Borrelia*.

9. The method according to claim 3, wherein the at least one antiparasitic drug comprises an antiparasitic drug selected from the group consisting of flubendazole and metronidazole.

10. The method according to claim 3, wherein said determining comprises detecting an emission of electromagnetic signals from bacterial DNA in a clinical specimen from the patient.

11. The method according to claim 10, wherein said determining comprises detecting a change in the emission of electromagnetic signals from bacterial DNA in a second clinical specimen from the patient.

12. A method of treating a patient having autistic spectrum disorder, consisting of:
   determining an infection in the patient by a bacteria of genus *Sutterella* and/or *Borrelia*, by an analysis of bacterial nucleic acids in blood of the patient;
   coadministering to the patient at least one antibiotic having a spectrum of activity against the bacteria of at least one of genus *Sutterella* and *Borrelia* and at least one antiparasitic drug, and optionally at least one antifungal drug, for 3 weeks per month during the first 3 months of coadministration;
   monitoring autistic behaviors of the patient during ongoing coadministration of the at least one antibiotic and the at least one antiparasitic drug to the patient; and
   modifying dosage of the at least one antibiotic in dependence on said monitoring.

13. The method according to claim 12, wherein said analysis of nucleic acids comprising performing polymerase chain reaction using a primer for a bacterial 16S ribosomal deoxyribonucleic acid sequence.

14. The method according to claim 12, wherein said analysis of nucleic acids comprises performing polymerase chain reaction using a primer specific for *Sutterella*.

15. The method according to claim 12, wherein said analysis of nucleic acids comprises performing polymerase chain reaction using a primer specific for *Borrelia*.

16. The method according to claim 12, wherein the at least one antibiotic comprises a tetracycline or a macrolide antibiotic.

17. The method according to claim 16, wherein the macrolide comprises azithromycin.

18. The method according to claim 12, wherein the method comprises coadministering at least one antifungal drug with the at least one antibiotic and the at least one antiparasitic drug.

19. The method according to claim 12, wherein said at least one antiparasitic drug comprises at least two different antiparasitic drugs.

20. The method according to claim 19, wherein the at least one antiparasitic drug comprises flubendazole and metronidazole.

* * * * *